US010758707B2

(12) United States Patent
Gläsel

(10) Patent No.: US 10,758,707 B2
(45) Date of Patent: Sep. 1, 2020

(54) MULTIPLE LUMEN MICROCATHETER TUBE AND METHOD FOR MANUFACTURING MULTIPLE LUMEN MICROCATHETER TUBES

(71) Applicant: Raumedic AG, Münchberg (DE)

(72) Inventor: Björn Gläsel, Kirchenlamitz (DE)

(73) Assignee: Raumedic AG, Münchberg (DE)

( * ) Notice: Subject to any disclaimer, the term of this patent is extended or adjusted under 35 U.S.C. 154(b) by 631 days.

(21) Appl. No.: 14/972,370

(22) Filed: Dec. 17, 2015

(65) Prior Publication Data

US 2016/0175558 A1 Jun. 23, 2016

(30) Foreign Application Priority Data

Dec. 19, 2014 (DE) .................. 10 2014 226 628

(51) Int. Cl.
*A61M 25/00* (2006.01)

(52) U.S. Cl.
CPC ........ *A61M 25/003* (2013.01); *A61M 25/001* (2013.01); *A61M 2025/0034* (2013.01); *A61M 2025/0037* (2013.01); *A61M 2025/0042* (2013.01)

(58) Field of Classification Search
CPC ........ A61M 2025/0042; A61M 1/1678; A61M 1/1682; A61M 1/3427; A61M 2025/0034; A61M 25/0068; A61M 25/0069; A61M 2025/0037; A61M 25/003; A61M 25/001; A61M 25/0043; A61M 25/007; A61M 25/0071; A61M 25/0026; A61M 2207/00; A61M 25/0015

USPC ...... 604/4.01, 6.16, 27, 29, 43, 48, 264, 278
See application file for complete search history.

(56) References Cited

U.S. PATENT DOCUMENTS

| | | | | |
|---|---|---|---|---|
| 4,274,417 A | * | 6/1981 | Delpy | A61M 25/0068 600/364 |
| 5,191,900 A | * | 3/1993 | Mishra | A61B 5/14528 422/947 |
| 5,195,962 A | * | 3/1993 | Martin | A61M 25/001 604/43 |
| 5,364,344 A | * | 11/1994 | Beattie | A61M 25/003 604/43 |
| 5,607,390 A | | 3/1997 | Patsalos et al. | |
| 5,718,678 A | * | 2/1998 | Fleming, III | A61M 25/0009 604/43 |
| 5,800,414 A | * | 9/1998 | Cazal | A61M 25/00 604/264 |
| 6,245,187 B1 | * | 6/2001 | Honsberg-Riedl | F16B 2/005 156/295 |
| 6,254,628 B1 | * | 7/2001 | Wallace | A61B 17/12118 606/108 |

(Continued)

FOREIGN PATENT DOCUMENTS

| | | |
|---|---|---|
| DE | 19714572 C1 | 6/1998 |
| DE | 693 23 563 | 9/1999 |

(Continued)

*Primary Examiner* — Scott J Medway
(74) *Attorney, Agent, or Firm* — Boyle Fredrickson S.C.

(57) ABSTRACT

A multiple-lumen microcatheter tube has at least two tube lumens and a closed distal tube end. In the area of the distal tube end, a separation strip has between the two tube lumens at least one passage opening. There results a multiple-lumen tube, whose use as for example a probe for measuring tissue parameters, is improved.

21 Claims, 4 Drawing Sheets

(56) References Cited

U.S. PATENT DOCUMENTS

| | | | | |
|---|---|---|---|---|
| 6,264,627 | B1* | 7/2001 | Liska | A61B 5/145 604/29 |
| 6,669,719 | B2* | 12/2003 | Wallace | A61B 17/12118 606/108 |
| 6,772,761 | B1* | 8/2004 | Rucker, Jr. | A61M 16/0666 128/207.14 |
| 6,929,618 | B1* | 8/2005 | Johansson | A61B 5/145 210/645 |
| 8,066,660 | B2* | 11/2011 | Gregersen | A61M 1/3653 604/29 |
| 8,333,740 | B2* | 12/2012 | Shippert | A61M 1/008 604/239 |
| 2004/0193098 | A1* | 9/2004 | Wentling | A61M 1/285 604/29 |
| 2005/0119597 | A1* | 6/2005 | O'Mahony | A61M 1/3413 604/4.01 |
| 2005/0137579 | A1* | 6/2005 | Heruth | A61M 5/14276 604/536 |
| 2005/0261663 | A1* | 11/2005 | Patterson | A61M 25/003 604/508 |
| 2006/0142703 | A1* | 6/2006 | Carter | A61M 25/0015 604/264 |
| 2006/0173440 | A1* | 8/2006 | Lamson | A61M 25/0068 604/506 |
| 2007/0255230 | A1* | 11/2007 | Gross | A61B 17/8811 604/272 |
| 2008/0082080 | A1* | 4/2008 | Braga | A61M 1/3661 604/523 |
| 2009/0118661 | A1* | 5/2009 | Moehle | A61M 25/0068 604/6.16 |
| 2009/0192435 | A1* | 7/2009 | Gregersen | A61M 1/3653 604/6.16 |
| 2009/0198219 | A1* | 8/2009 | Campbell | A61M 25/10 604/524 |
| 2009/0209940 | A1* | 8/2009 | Nimkar | A61M 25/001 604/523 |
| 2009/0216151 | A1* | 8/2009 | Speeg | A61B 10/0275 600/567 |
| 2010/0324503 | A1* | 12/2010 | McKinnon | A61M 25/0009 604/246 |
| 2011/0130745 | A1* | 6/2011 | Shevgoor | A61M 5/14 604/523 |
| 2011/0270368 | A1* | 11/2011 | Ginsburg | A61F 7/12 607/105 |
| 2012/0041419 | A1* | 2/2012 | Blanchard | A61M 25/0023 604/523 |
| 2012/0172791 | A1* | 7/2012 | Odland | A61M 1/0023 604/26 |
| 2017/0348512 | A1* | 12/2017 | Orr | A61M 1/0031 |

FOREIGN PATENT DOCUMENTS

| | | | |
|---|---|---|---|
| GB | 2130916 B * | 7/1986 | A61M 1/1678 |
| WO | 0103752 A1 | 1/2001 | |
| WO | 2004060465 A2 | 7/2004 | |
| WO | 2009095020 A1 | 8/2009 | |
| WO | 2014149708 | 9/2014 | |

* cited by examiner

MULTIPLE LUMEN MICROCATHETER TUBE AND METHOD FOR MANUFACTURING MULTIPLE LUMEN MICROCATHETER TUBES

CROSS-REFERENCES TO RELATED APPLICATIONS

This application claims the priority of German Patent Application, Serial no. 10 2014 226 628.9, filed Dec. 19, 2014, pursuant to 35 U.S.C. 119(a)-(d), the content of which is incorporated herein by reference in its entirety as if fully set forth herein.

FIELD OF THE INVENTION

The invention relates to a multiple-lumen micro-catheter tube with at least two tube lumens. The invention further relates to a method for manufacturing such a multiple-lumen micro-catheter tubes.

BACKGROUND OF THE INVENTION

Multiple-lumen tubes are known from WO 2014/149 708 A1. Such multiple-lumen can be used in medical technology as micro-tubes.

SUMMARY OF THE INVENTION

The object of the present invention is to further develop a multiple-lumen tube in such a manner that its parameters are improved, for example as a probe to measure tissue parameters.

This object is achieved by a multiple-lumen micro-catheter tube with the features specified in claim 1.

The inventive multiple-lumen tube micro-catheter allows conducting a medium through a lumen of the tube toward the distal end of the tube and through the at least one passage opening and through the other of the two tube lumens from the distal end of the tube back again. This allows conducting a diagnostic, analysis, or treatment medium to the place of use in the area of the distal end of the tube and can there possibly specifically interact with the tissue material. A proximal end of the tube may be in fluid communication with a supply or discharge device for supplying or discharging. A proximal end of the tube may be associated in fluid communication with a supply or discharge device for supplying or discharging a medium.

At least one window passage opening in at least one of the tube lumens, wherein between the at least one window passage opening a media exchange between the tube lumen and an environment is possible, ensures an intensive exchange interaction between at least one inner lumen of the tube lumens and a surrounding tube. The possibly multiple window passage openings can be designed as a measuring window. At least one window passage opening can be present in the two tube lumens. In this case, the window passage openings of the two tube lumens can be axially offset from one another in the direction of a longitudinal tube axis, which can increase the mechanical stability of the micro-catheter tube. The at least one window passage opening can be formed near the distal end of the tube. The multiple-lumen micro-catheter tube can have inner lumens with an inner diameter of 1 mm and less.

Just one window passage opening according to claim 3 reduces the manufacturing cost and allows reproducible conditions for media exchange. Alternatively, multiple window passage openings per tube lumen can be used. If one of the tube lumens has exactly one window passage opening, this can apply to all tube lumens. Alternatively, one of the tube lumens can have exactly one window passage opening and another tube lumen can have several window passage openings.

A permeable material according to claim 4 allows a defined exchange between a medium supplied and discharged through the tube lumen and an environment of the micro-catheter tube. The permeable material is permeable for the medium to be conducted in the micro-catheter tube. Alternatively or additionally, the permeable material can be permeable for the for the tissue material or blood surrounding the micro-catheter tube in the window passage opening. The permeable material can be a fibrous material. In the direction of the longitudinal axis the tube, i.e. axially, the permeable material can be longer than the associated window passage opening. In this way, an axial fixation of the permeable material in the pertinent tube lumen can be guaranteed.

An adhesive layer or glue layer according to claim 5 ensures a secure fixing of the permeable material. In addition, the adhesive layer can lead to a sealing of the permeable material toward an inner wall of the associated tube lumen. This forces a passage of the supplied or discharged fluid through the permeable material and avoids a short-circuit current between the tube lumen and the micro-catheter tube environment past the permeable material. The adhesive layer may be formed by a specific curable adhesive. The viscosity of the adhesive may be prior to curing in the range between 250 Pa-s and 400 Pa-s.

A fluid-tight closure of the distal end of the tube according to claim 6 avoids an unwanted media outlet at the distal end of the micro-catheter tube. Alternatively, the distal end of the tube can also be closed by a permeable material so that a distal opening of the micro-catheter tube can also be used as a measuring window. Such a closure by permeable material can be realized by a membrane-sealing plug or by a plug of fibrous material.

Inner diameters of the tube lumen according to claim 7 have been found particularly suitable for the particular application. The tube lumen can have the same inner diameter. However, this is not a compelling design.

A manufacturing method according to claim 8 can be realized with mass production methods. The multiple-lumen tube may be produced by extrusion. The window passage opening can be fitted by punching or cutting. When gluing the permeable material in the tube lumen, a capillary effect of the adhesive can be exploited. For this purpose, the viscosity or the amount of the adhesive can be adapted to the dimension of a gap between the tube lumen wall and the permeable material in the region of the respective window passage opening.

A manufacturing method according to claim 9 enables the formation of a passage opening between the remaining separating strip and the closure of the distal tube end, thus enabling an inter-lumen junction between the tube lumens of the multiple-lumen tubes, when this production process can also be realized with methods of mass production.

An occlusive adhesive according to claim 10 can have a viscosity in the range between 400 Pa-s and 800 Pa-s. When adhesively sealing the distal tube lumen, a capillary effect of the adhesive can be utilized in accordance with what has already been stated above in connection with the gluing of the permeable material.

The micro-catheter tube manufacturing methods which have been explained above may be combined.

The adhesive can in each case be dosed to the respective bonding position by means of an appropriate metering device. Such a metering device may be designed as a syringe.

BRIEF DESCRIPTION OF THE DRAWINGS

Embodiments of the invention will now be explained in detail based on the drawings. The figures show.

DETAILED DESCRIPTION OF THE PREFERRED EMBODIMENTS

Figure 12:
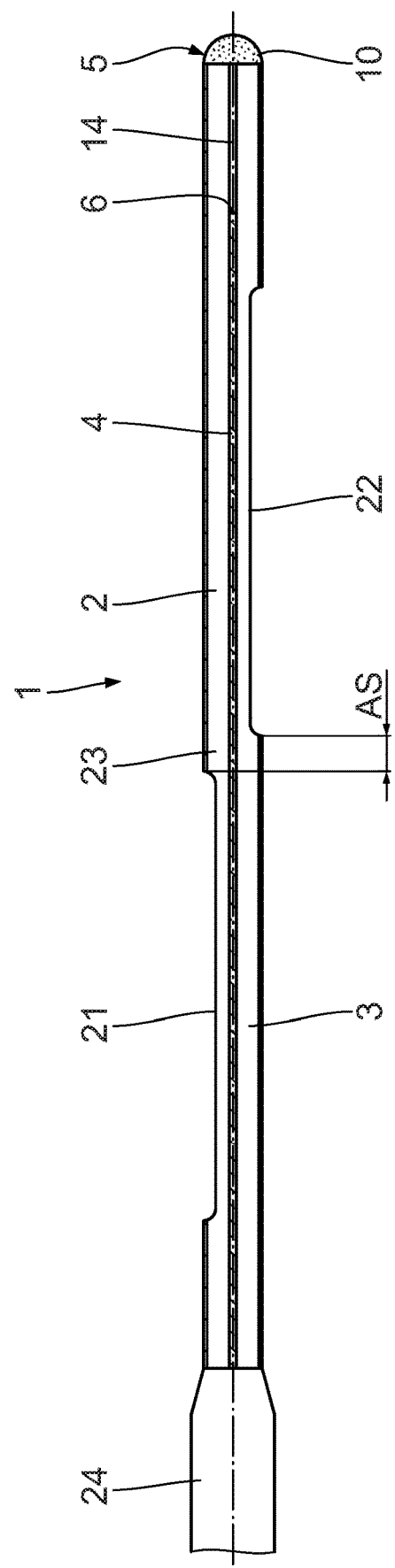
FIG. 12 shows in a representation similar to FIG. 4 the microcatheter tube with a further variant of embedded window passage openings, where opposite to the distal end of the tube, a connection adapter to a non-illustrated supply and discharge device of a catheter system is indicated.

A multiple-lumen micro-catheter tube 1 illustrated in FIG. 12 can be used as part of a dialysis probe. Such application is described in DE 693 23 563 T2.

The micro-catheter tube 1 is designed as a two-lumen tube. The micro-catheter tube 1 is made of a bondable carbon, for example, of a thermoplastic carbon. Examples include polyetherimide (PEI), polyether block amide (PEBA), polyamide (PA) or polysulfone (PSU). Copolymers of these materials can be also used.

The micro-catheter tube 1 has two tube lumens 2, 3. The tube lumens 2, 3 have an inner diameter in the range between 0.1 mm and 2 mm. In the illustrated example, the inner diameter is about 0.3 mm. A separating strip 4 between the two tube lumens 2, 3 has a minimum thickness of about 0.1 mm. Even lower minimum thicknesses are possible.

Not illustrated versions of the micro-catheter tube 1 can also have more than two tube lumens. The inner diameters of the tube lumens 2, 3 in the illustrated embodiment are equal. Also different inner diameters are possible.

Figure 1:
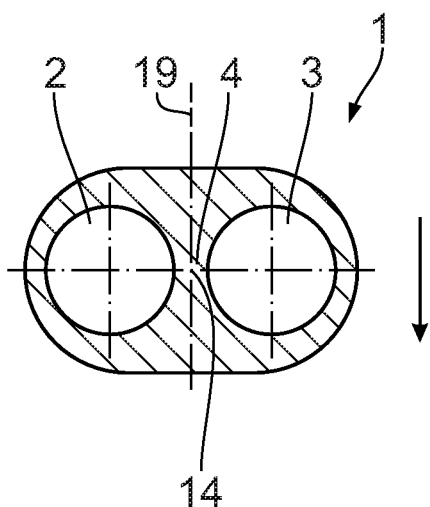
FIG. 1 shows a cross-section of a multiple-lumen micro-catheter tube using the example of a two-lumen tube.
Figure 2:
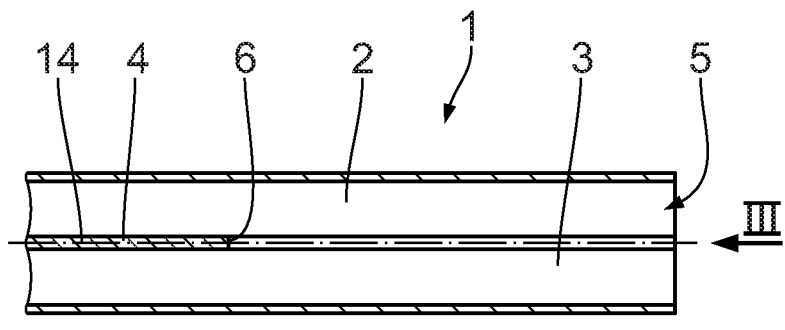
FIG. 2 shows an axial longitudinal section of the micro-catheter tube according to FIG. 1 in the area of a distal end of the tube.
Figure 3:
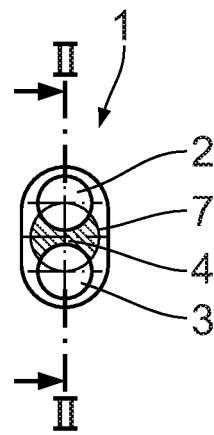
FIG. 3 shows a frontal view of the microcatheter tube in the viewing direction III from FIG. 2.

FIGS. 2 and 3 show the micro-catheter tube 1 in the region of a distal tube end 5. In this area, the separation strip 4 is removed so that an inter-lumen passage opening 6 results, which enables a media passage between the tube lumens 2 and 3. The removal of the separation strip 4 in the area of the distal end of the tube 5 can be done by removing material from the distal end side of the micro-catheter tube 1. This is indicated in FIG. 3 by a circular material removal area 7 covering the separation strip 3.

Figure 4:
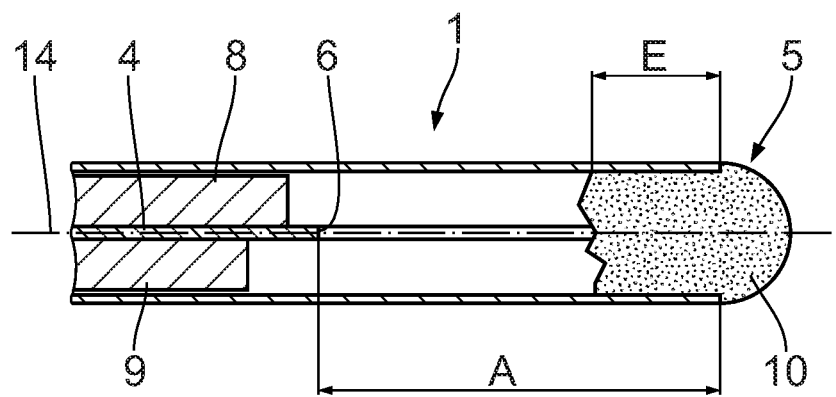
FIG. 4 shows in a representation similar to FIG. 2 the microcatheter tube with the distal tube end closed by means of an adhesive and the fiber material inserted into the two tube lumens.

FIG. 4 shows the micro-catheter tube 1 again in the region of the distal tube end 5 after performing additional manufacturing steps. Fiber material in the form of measuring fibers 8, 9 is introduced into the tube lumens 2 and 3 as a permeable material.

In addition, the distal end of the tube end 5 is hermetically sealed by an adhesive sealing plug 10. The latter has a penetration depth E into the distal end of the tube end 5, which is so low that the inter-lumen passage opening 6 is not closed by the adhesive sealing plug 10. A removal depth A of the separation strip 4 is therefore greater than the penetration depth E. After curing of the adhesive, the adhesive sealing plug 10 closes the distal end 5 in such a way that in the area of the adhesive sealing plug 10 an outer diameter of the micro-catheter tube 1 is not enlarged.

Figure 5:
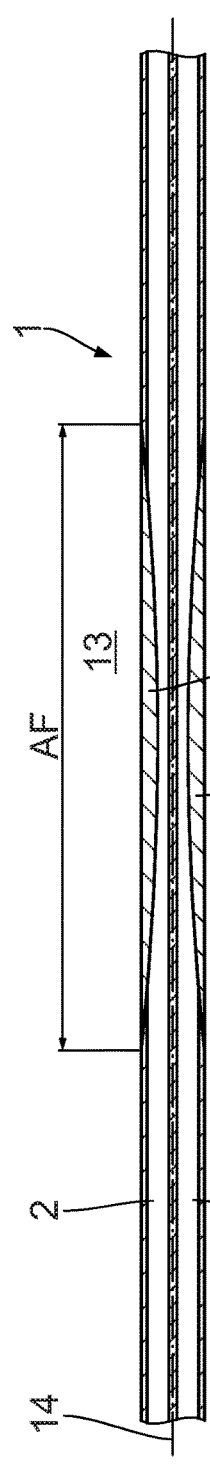
FIG. 5 shows in an axial longitudinal section a section of the microcatheter tube in the area of the window passage opening through which the media exchange between the tube lumen and an environment is made possible.

FIG. 5 shows a tube section of the micro-catheter tubes 1. This tube section can be in the region of the distal end of the tube; but this is not mandatory. The two tube lumens 2, 3 have in the area of this tube section in each case a window passage opening 11, 12, through which a media exchange between the tube lumens 2, 3 and an environment 13 of the micro-catheter tube 1 is enabled. In the embodiment of FIG. 5, each of the tube lumens 2, 3 has exactly one window passage opening 11, 12.

In an alternative, not illustrated embodiment, the micro-catheter tube 1 has at least one window passage opening exclusively in one of the two tube lumens 2 or 3. The introduction of the window passage openings 11, 12 can be performed by punching or cutting An axial extension AF of the window passage openings 11, 12, i.e. an extension along a longitudinal axis of the tube 14, is in the range between 2 mm and 30 mm, in particular in the range between 5 mm and 25 mm and can be for example 15 mm.

Figure 6:
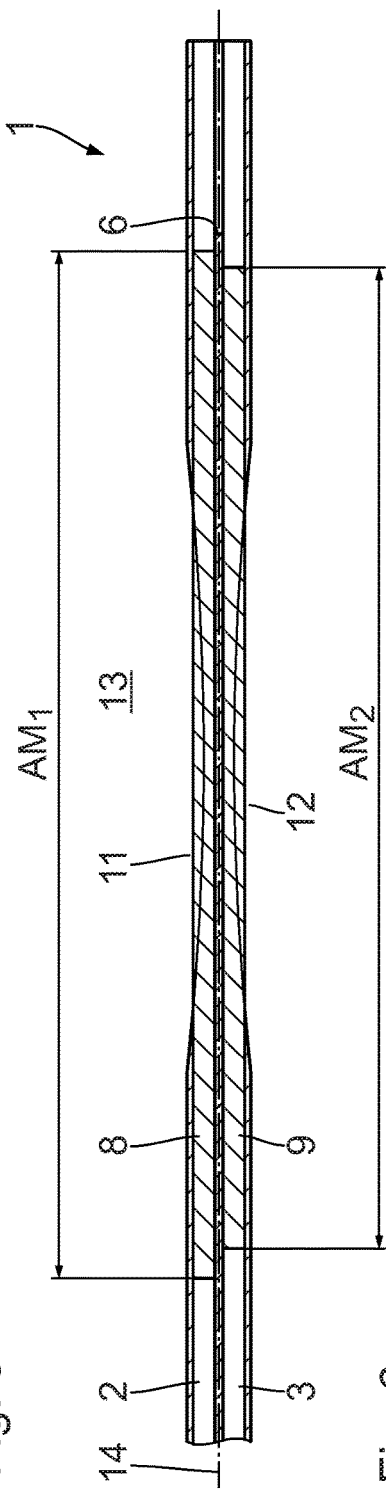
FIG. 6 shows in a representation similar to FIG. 5 the tube section after the introduction of the fiber material into the tube lumen at the level of the respective window passage opening
Figure 7:
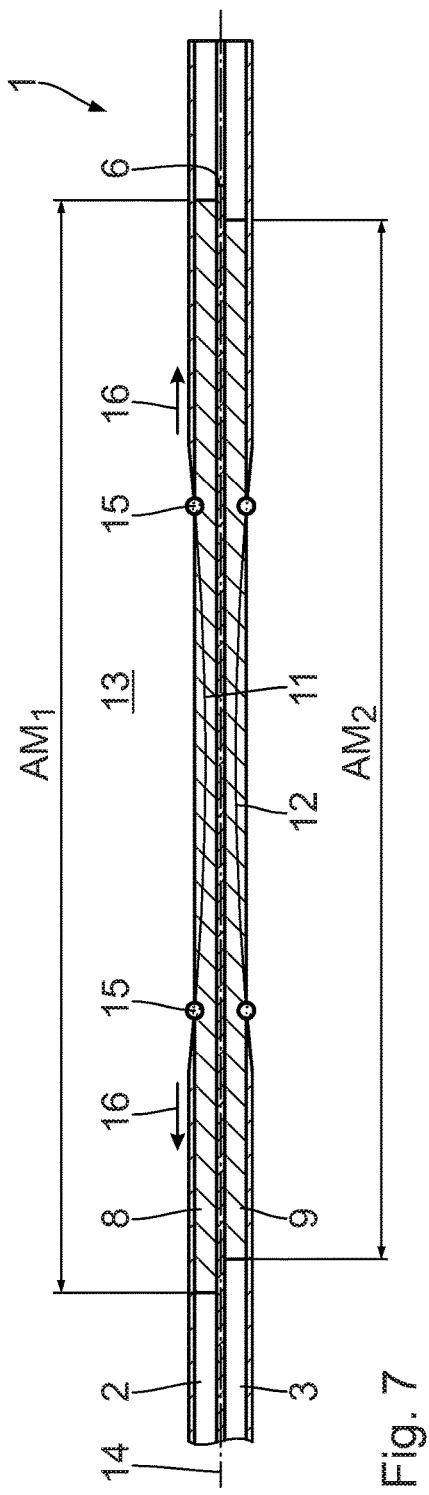
FIG. 7 shows in a representation similar to FIG. 6 the tube section after fixing of the fiber material in the tube lumen by gluing.

FIGS. 6 and 7 illustrate various manufacturing steps in the further fabrication of the tubes 1.

In the current representation according to FIG. 6, the measuring fibers 8 and 9 are inserted into the tube lumens 2, 3 each at the height of the window passage openings 11, 12. Axial extensions $AM_1$, $AM_2$ of the measuring fibers 8, 9 are greater than the axial extension AF of the measurement windows 11, 12. The axial extensions $AM_1$, $AM_2$ can differ from each other; but this is not mandatory. Since the axial extensions $AM_1$, $AM_2$ are greater than the axial extension AF, an insert position of the measuring fibers 8, 9 in the tube lumens 2, 3 can be guaranteed, in which the measuring fibers 8, 9 at their end protrude into the opening free lumen areas of tube lumens 2, 3, which favors an axial fixation of the measuring fibers 8, 9 in the tube lumens 2, 3 in the area of window passage openings 11, 12.

FIG. 7 shows the downstream manufacturing step in the further fixing of the measuring fibers 8, 9 in the tube lumens 2, 3 by gluing. For this purpose, first a liquid, curable adhesive is applied to bonding positions 15; the adhesive's viscosity and quantity is matched to a measure of an adhesive gap between an inner tube lumen wall and the measuring fibers 8, 9. Seen in a section perpendicular to the longitudinal axis of tube 14, this adhesive gap has a gap area in the range between 0.01 $mm^2$ and 0.1 $mm^2$, for example, a gap area of 0.04 $mm^2$ Due to the adjusted viscosity, the adhesive is drawn in by capillary action in the direction of arrows 16 in FIG. 7 into the opening-free regions of the tube lumens 2, 3 adjacent to the window passage openings 11, 12 and surrounds the measuring fibers 8, 9 then fully, i.e. annularly, such that the measuring fibers 8, 9 are sealed on their shell-side fluid-tight against the respective inner wall of the tube lumens 2, 3.

The quantity of the adhesive is so adjusted that the adhesive does not penetrate up to the front ends of the measuring fibers 8, 9 so that an undesired closing of this front-face of the measuring fiber ends by the adhesive is prevented.

The adhesive is a targeted curable adhesive substance, for example, an adhesive curable under UV radiation, in particular cyanoacrylate. The adhesive may have a viscosity in the range from 2,500 cP to 4,000 cP (2.5 Pa-s to 4.0 Pa-s) or is in the range between 250 and 400 Pa-s. Alternatively or in addition to UV curing, an adhesive can also be used, in which the curing effect occurs by other influence parameters, for example, by a temperature-controlled curing, a humidity-controlled curing or a purely time-controlled curing.

For closing the distal end of the tube 5 by means of adhesive sealing plug 10 is also used an adhesive adjusted in terms of its amount and viscosity, which in particular is adjusted to the inside diameter of the micro-catheter tube 1 in the region of the distal tube end 5. There, the inner diameter, compared to the inter diameter of the tube lumens 2, 3, is increased due to the removal of the separation strip 4, and perpendicular to the separation strip 4 is more than twice as large than the inner diameter of each of the tube lumens 2, 3. The viscosity of the adhesive for the adhesive sealing plug 10 is adjusted so that there results the penetration depth E, which is smaller than the depth A of the removed separation strip 4. The adhesive is applied to the distal tube end 5 which has an area between 0.1 mm$^2$ and 0.5 mm$^2$ and can be, for example, 0.20 mm$^2$ The viscosity of the adhesive for the adhesive sealing plug 10 lies in the range between 4,000 cP and 8,000 cP (4.0 Pa-s to 8.0 Pa-s) or in the range between 400 and 800 Pa-s. For the bonding of the measuring fibers 8, 9 is thus in particular used a different adhesive than for the preparation of the adhesive sealing plug 10.

FIGS. 8 to 12 show further variants of window passage opening that can be used instead of the window openings 11, 12. The components which correspond to those which have already been explained above in reference to FIGS. 1 to 7 have the same reference numerals and will not be discussed again in detail.

Figure 8:
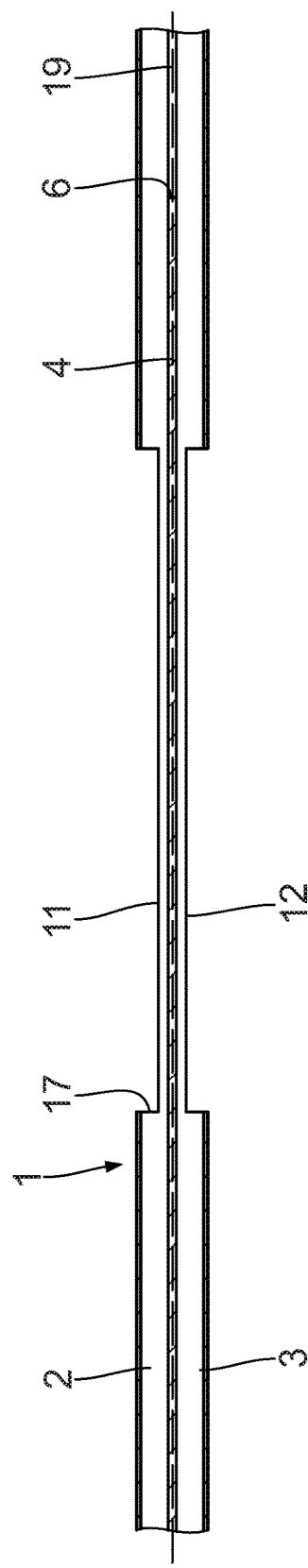
FIGS. 8 to 10 show in a representation similar to FIG. 5 the tube section including the distal tube end with further variants of embedded windows-passage openings.

In the micro-catheter tube according to FIG. 8, the window passage openings 11, 12 are designed as punched components with sharp, axial-end stages 17.

Figure 9:
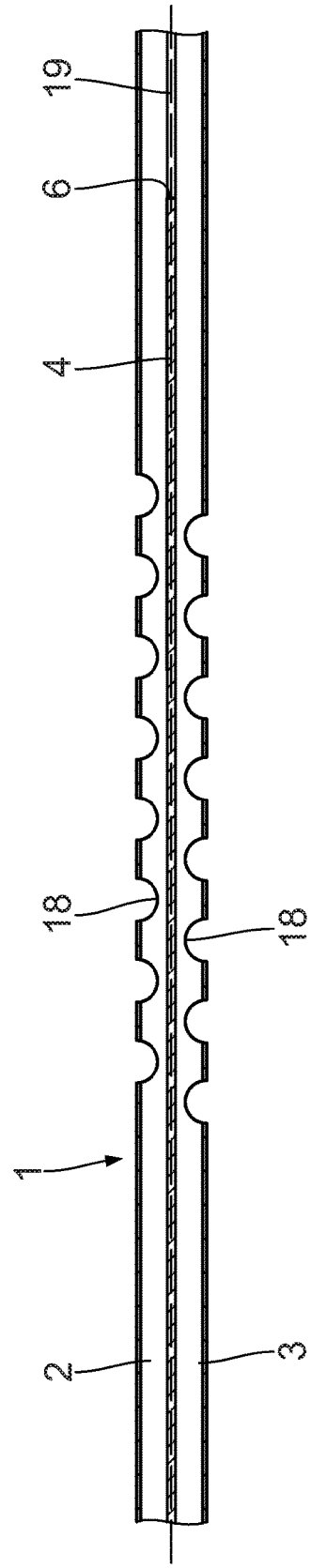

In the micro-catheter tube 1 according to FIG. 9, each of the tube lumens 2, 3 has a plurality, namely by way of example shown eight, window passage openings 18. These are designed as edge-side punchings in the outer walls of the tube lumens 2, 3, wherein the punching movement runs parallel to a separation plane 19 defined by the course of the separation strip 4 (see FIGS. 1 and 9), i.e. perpendicular to the drawing plane of FIG. 9.

Figure 10:
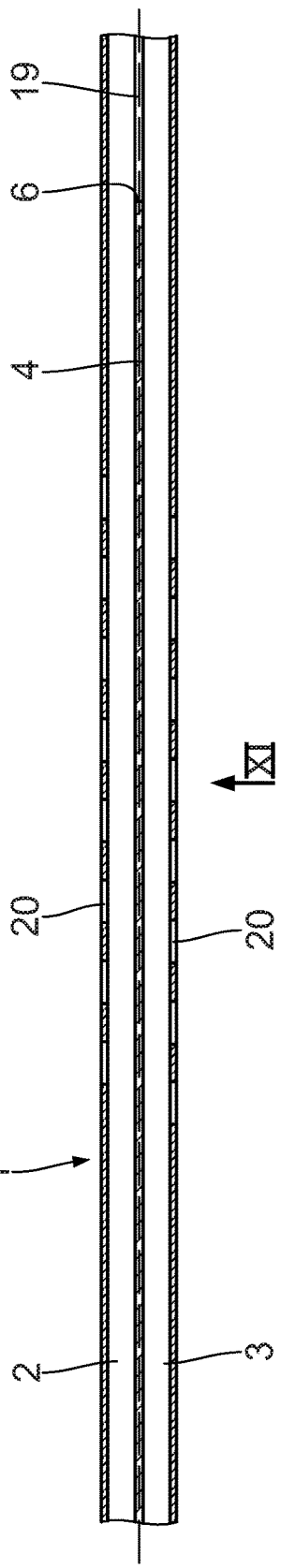
Figure 11:
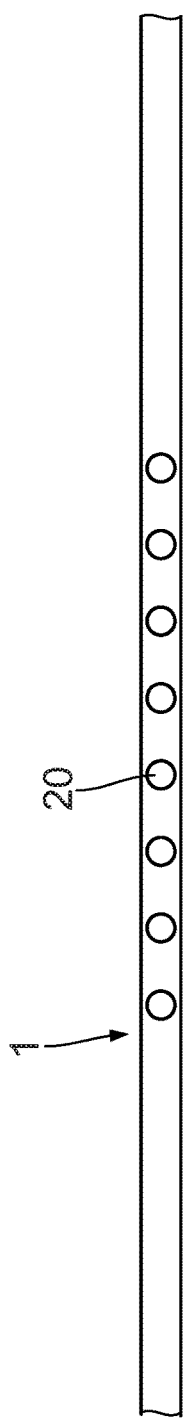
FIG. 11 shows a side view of the tubular section according to FIG. 10 from the viewing direction XI in FIG. 10.

In manufacturing the micro-catheter tube 1 and according to FIGS. 10 and 11, the window passage openings 20 are produced by cutting or punching with a cutting motion perpendicular to the parting plane 19.

FIG. 12 shows a variant of the micro-catheter tubes 1 with two axially staggered window passage openings 21, 22 which with respect to their axial extension correspond to the window passage openings 11, 12 according to FIGS. 5 and 8. The axial staggering of the window passage openings 21, 22 to each other is so great that the window passage openings 21, 22 do not axially overlap.

There thus remains in the axial direction between the window passage openings 21, 22 a tube ring 23 with an axial extension AS. Such an axial staggering of the window passage openings 21, 22 increases the mechanical stability of the micro-catheter tube 1.

In addition, in FIG. 12 at the end section of the micro-catheter tube 1 opposite to the distal tube end 5 is indicated a section of the connection adapter 24. The connection adapter 24 is thus attached to the proximal end of the micro-catheter tube 1. Through the connection adapter 24, this proximal tube end can be in fluid communication with a supply and discharge device for supplying or discharging a medium.

The invention claimed is:

1. A multiple-lumen microcatheter tube comprising:
   at least two tube lumens;
   a closed distal tube end;
   a separation strip and at least one passage opening disposed between and fluidically connecting the two tube lumens,
   wherein the at least one passage opening enables a media passage between the tube lumens;
   wherein at least one of the tube lumens comprises at least one window passage opening, through which is made possible a medium exchange between the tube lumens and an environment; and
   wherein a permeable material is introduced into the tube lumen in an area of the window passage opening, wherein the permeable material is a fibrous material in the form of a plurality of fibers, and wherein, in direction of a longitudinal axis of the tube, the permeable material is axially longer than the associated window passage opening.

2. The microcatheter tube according to claim 1, wherein at least one of the tube lumens comprises a plurality of window passage openings.

3. The microcatheter tube according to claim 1, wherein at least one of the tube lumens comprises exactly one window passage opening.

4. The microcatheter tube according to claim 1, comprising an adhesive fixing the permeable material in the tube lumen.

5. The microcatheter tube according to claim 1, wherein the distal tube end is fluid-tightly closed.

6. The microcatheter tube according to claim 1, wherein the tube lumens have an inner diameter in the range between 0.1 mm and 2 mm.

7. A method for manufacturing of a multiple-lumen microcatheter tube comprising:
   producing a multiple-lumen tube comprised of a plurality of tube lumens,
   introducing at least one window passage opening into at least one of the tube lumens,
   inserting a permeable material into the at least one tube lumen comprising the at least one window passage opening at the height of the window passage opening, wherein the permeable material is a fibrous material in the form of a plurality of fibers, and wherein, in direction of a longitudinal axis of the tube, the permeable material is axially longer than the associated window passage opening,
   fixing the permeable material in the at least one tube lumen comprising the at least one window passage opening by gluing, providing the multiple-lumen tube having a distal tube end, removing a separation strip section between two of the tube lumens in the area of the distal tube end, and closing the distal tube end.

8. The method according to claim 7, wherein closing of the distal tube end occurs by gluing.

9. The method according to claim 7, wherein closing of the distal tube end occurs by insertion of a permeable material in the distal tube end.

10. The method according to claim 7, wherein closing of the distal tube end occurs by fixing of a permeable material received in the distal tube end.

11. The method according to claim 7, wherein removing the separation strip section between the two of the tube lumens opens at least one inter-lumen passage opening extending between the two of the tube lumens.

12. The microcatheter tube according to claim 1, wherein the at least one passage comprises at least one inter-lumen passage extending between the two tube lumens that is opened when the separation strip is removed.

13. The microcatheter tube according to claim 1, wherein the at least one passage comprises at least one inter-lumen passage extending between the two tube lumens that is opened when the separation strip is removed.

14. The microcatheter tube according to claim 1, wherein a distal end of the microcatheter tube is substantially fluid-tightly closed.

15. The microcatheter tube according to claim 1, wherein the permeable material is fixed to the at least one of the tube lumens having the at least one window passage formed therein.

16. The microcatheter tube according to claim 15, wherein a permeable material is disposed at a distal end of the microcatheter tube closing the distal end of the microcatheter tube.

17. The microcatheter tube according to claim 1, wherein the at least one passage opening is positioned in the area of a distal tube end.

18. The method according to claim 7, wherein the glue is added in a liquid state and drawn into opening-free regions of the tube lumens adjacent to the window passage opening by a capillary action.

19. The method according to claim 18, wherein the glue, after being drawn into the opening-free regions of the tube lumens, surrounds the permeable material annularly such that the permeable material is sealed fluid-tightly against an inner wall of the at least one tube lumen.

20. The microcatheter tube according to claim 4, wherein the adhesive surrounds the permeable material annularly such that the permeable material is sealed fluid-tightly against an inner wall of the at least one tube lumen.

21. The microcatheter tube according to claim 1, wherein the fibrous material fills up the complete cross section of the tube lumen in the region of the associated window passage opening.

* * * * *